United States Patent
Stein-Konertz et al.

(10) Patent No.: US 7,438,850 B2
(45) Date of Patent: Oct. 21, 2008

(54) STERILIZATION METHOD FOR THE PRODUCTION OF IMPLANTABLE OR TRANSPLANTABLE BIOLOGICAL MATERIAL

(75) Inventors: Marita Stein-Konertz, Berlin (DE); Wilhelm Erdbrügger, Berlin (DE)

(73) Assignee: AutoTissue GmbH (DE)

( * ) Notice: Subject to any disclaimer, the term of this patent is extended or adjusted under 35 U.S.C. 154(b) by 36 days.

(21) Appl. No.: 11/663,443

(22) PCT Filed: Sep. 8, 2005

(86) PCT No.: PCT/DE2005/001595

§ 371 (c)(1), (2), (4) Date: Mar. 20, 2007

(87) PCT Pub. No.: WO2006/032240

PCT Pub. Date: Mar. 30, 2006

(65) Prior Publication Data

US 2008/0089806 A1    Apr. 17, 2008

(30) Foreign Application Priority Data

Sep. 22, 2004  (DE) ........................ 10 2004 047 247

(51) Int. Cl.
*A61L 2/18*    (2006.01)
(52) U.S. Cl. ............................ 422/28; 422/1; 623/915; 623/920

(58) Field of Classification Search .................... 422/1, 422/28; 623/915, 920
See application file for complete search history.

(56) References Cited

U.S. PATENT DOCUMENTS 7,014,655 B2    3/2006  Barbarash et al.

FOREIGN PATENT DOCUMENTS

| DE | 100 60 660 | 6/2002 |
| EP | 0 889 690 B1 | 2/2003 |
| WO | WO 97/36479 | 10/1997 |

*Primary Examiner*—Jill Warden
*Assistant Examiner*—Sean E. Conley
(74) *Attorney, Agent, or Firm*—Wood, Phillips, Katz, Clark & Mortimer

(57) ABSTRACT

The sterilization of biological material of animal or human origin, which is to be used as an implant or transplant, is performed according to a validated sterilization method with a margin of safety of $10^6$ germs by which harmful microorganisms are physically separated and chemically sterilized in four successive steps, initially in an antibiotic, then in deoxicholic acid, then in a surface-active substance and finally in primary alcohol, respectively accompanied by rinsing steps involving an aqueous solution after steps two to four. A bioprosthesis sterilized with a margin of safety>$10^6$ germs can be implanted without any further treatment, does not have a tendency towards calcification, and ensures a long service life.

6 Claims, No Drawings

STERILIZATION METHOD FOR THE PRODUCTION OF IMPLANTABLE OR TRANSPLANTABLE BIOLOGICAL MATERIAL

This invention relates to a sterilization method for the production of implantable or transplantable biological material of animal or human origin.

For quite some time now, there have been manifold efforts to sterilize xenogenic or allogenic material and use it as an implant or transplant. For example, it is known that biological heart flaps from foreign material obtained from pigs, cows, or horses are produced using glutaraldehyde that seals the cell surface and also has a germicidal, sterilizing effect. Bioprostheses produced in this way meet the mandatory sterility requirements but comprise the setback that, dependent on the patient's age, gradual calcification may occur which may render the bioprosthesis inoperative.

It is the object of this invention to state a method of sterilizing biological material of animal or human origin for providing biological implants or transplants that is validated by international standards, requires little effort, and poses no risks with regard to harmful microorganisms or later calcification.

This object is achieved according to the invention by a method comprising the characteristics described in claim 1. The dependent claims disclose further characteristics and advantageous improvements of the invention.

The basic inventive idea is that the animal source material is treated in a combination of four successive procedural steps, each of which being effective in a specific time interval, first in an antibiotic solution, then in a deoxycholic acid solution, then in a surface-active substance, and finally in a primary alcohol. The sterilizing substance used in each step has both a physical, i.e. a separating and removing, and a chemical sterilization effect on the respective micro-organisms. The second to fourth treatment steps are each followed by a rinsing process with an aqueous solution, preferably a sodium chloride solution, to remove the sterilizing agent and the separated microorganisms. It is important to perform the sterilization and rinsing steps in the specified sequence and in a specific time interval.

The proposed sterilization method ensures sterilization of the source material that meets international standards and achieves a required margin of safety of $>10^6$ germs. The biomatter sterilized in this way can be implanted (or transplanted) into the human body without any safety risk. Since the sterilization method according to the invention also separates phospholipides that are responsible for calcification from the material, risk of calcification is clearly reduced. Implant or transplant life is increased.

An embodiment of the method according to the invention will be explained in greater detail using the example of producing heart flap implants from porcine material.

In a first procedural step, an aorta flap taken from a pig, cut to size and freed of fat, is kept for a specific time in an antibiotic solution that suppresses the growth of bacteria and fungi. At the same time, physical separation effects are achieved for reducing the number of microorganisms. The antibiotic solution may contain, for example, penicillin, streptomycin, and amphotericin.

In the subsequent second procedural step, the aorta flap previously treated with the antibiotic is held into a solution of deoxycholic acid in physiological saline. Sodium deoxylate has a decellularizing effect, i.e. an effect that kills and separates the cells that are present in the tissue, and also an antibiotic effect for further prevention of microorganism growth.

Following these first two steps, the aorta flap is rinsed multiple times in an aqueous solution to rinse off the deoxycholic acid and superficial germs.

In the subsequent (third) procedural step, the aorta flap is introduced to a surface-active substance, namely, a lipoprotein that has hemolytic, antiviral, and antibacterial properties and—in addition to its chemical effect—comprises a physical effect that influences the attachment and separation of the microorganisms.

The lipoprotein treatment is again followed by multiple rinsing processes with an aqueous solution to rinse off any remaining detergents from the previous step and to reduce the number of germs at the same time.

The next—fourth—procedural step involves treating the aorta flap with a primary alcohol such as 70% ethanol that acts on vegetative cells of bacteria and fungi as well as on viruses comprising a coat. Furthermore, phospholipides that may still be present and are mainly responsible for calcification of the biological implant are removed from the cell membrane. The chemical effect is once again accompanied by physical separation processes when the porcine heart flap is located in the treatment chemical.

This fourth treatment step is again followed by a multiple rinsing step in an aqueous solution to balance the water household of the tissue that was dehydrated by the alcohol and to use the diluting effect to further reduce the portion of bacteria and fungi.

As a result of the treatment steps described above for sterilizing a porcine aorta flap, a bioprosthesis is obtained that is sterile according to European standards and can be implanted without any further treatment.

The sterilizing effect of the procedure and compliance with the respective sterility limits based on European standard ISO 14160 is confirmed by accredited testing centers. A test of this sterilization method found that it is due to the combined—chemical (killing) and physical (separating and removing)—effects of the chemical sterilization agents used in each treatment step that a margin of safety according to the European standard of more than $10^6$ germs is achieved.

The invention claimed is:

1. A sterilization method for producing transplantable or implantable biological material of animal or human origin, characterized in that it comprises four sterilization steps that succeed one another in the sequence given below and have a combined chemical and physical effect:
   1. Treatment of the source material in an antibiotic solution to prevent the growth of microorganisms and to separate them;
   2. Further treatment of the material in deoxycholic acid to prevent the growth of microorganisms and to separate them, in combination with a downstream first rinsing process in an aqueous solution for removing the deoxycholic acid and for rinsing the separated microorganisms from the surface;
   3. Further treatment of the material in a surface-active lipoprotein solution with a hemolytic, antibacterial, antiviral, and separating effect on the microorganisms and for further removal of the deoxycholic acid, in combination with a subsequent second rinsing process in aqueous solution; and 4. Further treatment of the material in primary alcohol with a fungicidal, bactericidal, and antiviral effect for further combined separation and complete destruction of the microorganisms, in combination with a subsequent third rinsing process in aqueous solution.

2. The method according to claim 1 wherein the four sterilization steps and the rinsing steps are performed in a specified time interval.

3. The method according to claim 1 wherein 70% ethanol is used as the primary alcohol.

4. The method according to claim 1 wherein one rinsing process includes multiple successive rinsing steps.

5. The method according to claim 1 wherein the chemically and physically acting sterilization agents used in sterilization steps 1 to 4 are dissolved in a sodium salt solution.

6. The method according to claim 1 wherein an aqueous sodium salt solution is used as a detergent.

* * * * *